(12) United States Patent
Dougal (10) Patent No.: US 7,730,893 B2
(45) Date of Patent: Jun. 8, 2010

(54) ELECTROMAGNETIC RADIATION THERAPY

(75) Inventor: Gordon Rex Paterson Dougal, Durham (GB)

(73) Assignee: 1072 Technology Limited, Durham (GB)

(*) Notice: Subject to any disclaimer, the term of this patent is extended or adjusted under 35 U.S.C. 154(b) by 0 days.

(21) Appl. No.: 11/155,431

(22) Filed: Jun. 17, 2005

(65) Prior Publication Data
US 2005/0234383 A1 Oct. 20, 2005

Related U.S. Application Data

(63) Continuation of application No. 09/529,210, filed as application No. PCT/GB98/03073 on Oct. 12, 1998, now abandoned.

(30) Foreign Application Priority Data

| Oct. 10, 1997 | (GB) | ................................. 9721506.5 |
| Dec. 31, 1997 | (GB) | ................................. 9727441.9 |

(51) Int. Cl.
  *A61B 19/00* (2006.01)
  *A61N 5/06* (2006.01)
(52) U.S. Cl. ........................................ 128/898; 607/88
(58) Field of Classification Search ................ 128/898; 607/88–94; 606/3, 9
See application file for complete search history.

(56) References Cited

U.S. PATENT DOCUMENTS

| 4,878,891 | A | * | 11/1989 | Judy et al. .................. 604/5.02 |
| 4,917,084 | A | * | 4/1990 | Sinofsky ......................... 606/7 |
| 4,930,504 | A | * | 6/1990 | Diamantopoulos et al. ..... 607/88 |
| 4,951,663 | A | * | 8/1990 | L'Esperance, Jr. ............ 607/89 |
| 5,066,291 | A | * | 11/1991 | Stewart .......................... 606/3 |
| 5,259,380 | A | | 11/1993 | Mendes et al. .............. 607/115 |
| 5,348,551 | A | * | 9/1994 | Spears et al. ................... 606/5 |
| 5,445,146 | A | | 8/1995 | Bellinger ..................... 607/89 |
| 5,464,436 | A | | 11/1995 | Smith ........................... 607/89 |
| 5,500,009 | A | * | 3/1996 | Mendes et al. ................ 607/88 |
| 5,527,350 | A | | 6/1996 | Grove et al. ................... 606/3 |
| 5,630,811 | A | | 5/1997 | Miller ........................... 606/9 |
| 5,658,323 | A | | 8/1997 | Miller ........................... 606/9 |
| 5,707,403 | A | | 1/1998 | Grove et al. ................... 606/3 |
| 5,743,901 | A | | 4/1998 | Grove et al. ................... 372/72 |
| 5,818,048 | A | * | 10/1998 | Sodickson et al. ........... 250/343 |
| 5,849,035 | A | * | 12/1998 | Pathak et al. ................ 128/898 |
| 5,868,731 | A | * | 2/1999 | Budnik et al. .................. 606/9 |
| 5,989,245 | A | | 11/1999 | Prescott ....................... 606/14 |
| 6,027,495 | A | | 2/2000 | Miller ........................... 606/9 |
| 6,063,108 | A | * | 5/2000 | Salansky et al. ............. 607/89 |
| 6,179,830 | B1 | * | 1/2001 | Kokubu ........................ 606/16 |
| 6,471,716 | B1 | * | 10/2002 | Pecukonis .................... 607/89 |
| 2005/0234383 | A1 | * | 10/2005 | Dougal ...................... 604/5.02 |

FOREIGN PATENT DOCUMENTS

| EP | 0533585 B1 | 3/1993 |
| WO | WO98/23329 | 6/1998 |

OTHER PUBLICATIONS

Spicer et al.; Lasers in Dermatology, Journal of the American Academy of Dermatology, Jan. 1996.*
Stellar et al.; Lasers in Surgery, LaserApplications in Medicine and Biology, vol. 2, 1974 pp. 246-249.*
Abergel et al., "Laser Treatment of Keloids: A Clincal Trial and an In Vitro Study with Nd:YAG Laser," Lasers in Surgery and Medicine 4: 291-295, 1984.
Abergel et al., "Nonthermal Effects on Nd:YAG Laser on Biological Functions of Human Skin Fibroblasts in Culture," Lasers in Surgery and Medicine 3: 279-284, 1984.
Almeida-Lopes et al., "Comparison of the Low Level Laser Therapy Effects on Cultured Human Gingival Fibroblasts Proliferation Using Different Irradiance and Same Fluence", Lasers in Surgery and Medicine 29:179-184, 2001.
Castro et al., "Effects of the Nd:YAG Laser on DNA Synthesis and Collagen Production in Human Skin Fibroblast Cultures," Annals of Plastic Surgery, vol. 11, No. 3, pp. 214-222, 1983.
Kreisler et al., "Low Level 809-nm Diode Laser Induced In Vitro Stimulation of the Proliferation of Human Gingival Fibroblasts," Lasers in Surgery and Medicine 30:365-369, 2002.
Loevschall et al., Effect of Low Level Diode Laser Irradiation of Human Oral Mucosa Fibroblasts in Vitro, Lasers in Surgery and Medicine 14:347-354, 1994.
Mokhtar et al., "Double-Blind, Placebo-Controlled Investigation of the Effect of Combined Phototherapy/Low Intensity Laser Therapy Upon Experimental Ischaemic Pain in Humans," Lasers in Surgery and Medicine 17:74-81, 1995.
Pereira et al., "Effect of Low-Power Laser Irradiation on Cell Growth and Procollagen Synthesis of Cultured Fibroblasts", Lasers in Surgery and Medicine 31:263-267, 2002.

(Continued)

*Primary Examiner*—Ahmed M Farah
(74) *Attorney, Agent, or Firm*—Myers Bigel Sibley & Sajovec (57) ABSTRACT

An electromagnetic radiation therapy system comprises means for emitting divergent electromagnetic radiation having a wavelength between 950 and 1500 nm and being capable of producing, at the site being treated, a radiation intensity of at least 50 μWatts/cm$^2$. Also disclosed are the use of the system for treating various conditions and the method of applying the treatment.

27 Claims, 9 Drawing Sheets

OTHER PUBLICATIONS

Sakihama, Hideki, "Effect of a Helium-Neon Laser on Cutaneous Inflammation," The Kurame Medical Journal, vol. 42, p. 299-305, 1995.

Vecchio et al., "A Double-Blind Study of the Effectiveness of Low Level Laser Treatment of Rotator Cuff Tendinitis," British Journal of Rheumatology 1993: 32:740-742.

* cited by examiner

Fig. 1
PLAN VIEW

Fig. 2
SIDE VIEW

Fig. 3
UNDERSIDE PLAN VIEW

END VIEW

REAR VIEW

PANEL A PLAN VIEW

PANEL A' SIDE VIEW

Fig. 14

ELECTROMAGNETIC RADIATION THERAPY

RELATED APPLICATIONS

This is a continuation application of and claims the benefit of priority from U.S. patent application Ser. No. 09/529,210, filed Jul. 24, 2000 (abandoned), which is a National Phase application of International Application Ser. No. PCT/GB98/03073, filed Oct. 12, 1998 and published as PCT Publication No. WO 99/19024, which claims priority from Great Britain Patent Application Serial No. 9721506.5 filed Oct. 10, 1997, and Great Britain Patent Application Serial No. 9727441.9, filed Dec. 31, 1997, the disclosures of which are incorporated herein by reference in their entireties.

FIELD OF THE INVENTION

This invention relates to an apparatus producing, and a method of therapy using, electromagnetic radiation for the treatment of diseases and for the maintenance or improvement of org or body tissues, including muscles. The invention may be used in connection with the cure or alleviation of a variety of diseases including infectious diseases and pathological processes including those caused by viruses and bacteria.

By way of example, the invention may be used in connection with diseases caused by the herpes virus which is known to be responsible for a number of common ailments including corneal dendritic ulcers, genital herpes, herpes labialis (cold sores), herpes zoster (shingles) and herpes stomatitis. These infections tend to be recurrent and are not cured by existing, medically accepted treatments.

BACKGROUND OF THE INVENTION

Current medically accepted methods of treating infections caused by the herpes virus are chemotherapeutic agents which are applied topically, injected or taken orally. Such treatment can often deal with the immediate infection but does not prevent a recurrence of the infection at a later date after the treatment has ceased.

It has been known for several decades that the use of light can give a positive therapeutic effect in the treatment of a wide spectrum of diseases. In the 1960's the use of narrow wavelength light was investigated in vivo/in vitro experiments. It was found that light of wavelength greater than 440 nm did not work. Further investigations were carried out with light having a wavelength of from 300 to 350 nm (UV light) but it was found that infection was exacerbated/promoted rather than ameliorated/eliminated. Some attempts have been made to treat individuals affected with the herpes virus by treatment with light of the wavelength 660 nm, as described in U.S. Pat. No. 5,500,009. However, the present inventor was unable to achieve a significant clinical outcome or benefit at that wavelength.

Additionally, it is known from the prior art to use a laser to produce coherent radiation and to focus it on the area to be treated. Nd YAG laser treatment at a fundamental wavelength of 1064 nm is associated with decreased pain, scarring and improved healing (U.S. Pat. No. 5,445,146). Additionally it has been reported that diodes emitting light at the red wavelength, 940±25 nm can be used to treat a range of essentially musculoskeletal ailments (U.S. Pat. No. 5,259,380). However there is no indication that light of a wavelength above this would be of any therapeutic use.

It has now been surprisingly established that low intensity electromagnetic radiation of small bandwidth is effective in the treatment of infectious diseases, inflammatory-type diseases and other conditions, including the alleviation of pain. It is postulated that the way in which the electromagnetic radiation effects its action is by way of energy transmission through cellular components/organelles.

A water molecule that has a range of electromagnetic radiation wavelengths passed through it will produce several transmission peaks. These transmission peaks are associated with the preferred therapeutic electromagnetic radiation wavelength range of the invention and thus implies a role for the water molecule in the general mechanism of action.

STATEMENTS OF THE INVENTION

According to the present invention there is provided an electromagnetic radiation therapy system comprising means for emitting divergent electromagnetic radiation between 980 and 1500 nm and being capable of producing, at the site being treated, a radiation intensity of at least 50 $\mu$Watts/cm$^2$ and up to 2 Watts/cm$^2$.

Reference herein to a site being treated is intended to include, without limitation, the skin or musculature or internal organ of a human or animal subject.

Preferably the wavelength of the electromagnetic radiation is in the range 980 nm-1300 nm. A particularly preferred wavelength is at, or about, 1072 nm. A yet further particularly preferred wavelength is at, or about, 1268 nm.

Our studies have shown that the wavelength centred around 1072 nm is particularly effective at treating herpetic and bacterial infections, alleviating acute pain and in treating eye conditions, whilst the wavelength centred around 1268 nm is particularly effective at providing pain relief from deep muscle injury. It is of note that these two preferred wavelengths correspond to the peak emission wavelengths of a water molecule light transmission profile and thus we believe that the mechanism of action is related to water and possibly cell membranes.

By divergent it is meant that the electromagnetic radiation emitted from the system of the invention has a divergent half angle of at least 5°. Preferably divergence of the elctromagnetic radiation is in the range 15° to 45° half angled divergent.

Preferably the electromagnetic radiation is continuous or pulsed.

Preferably when the electromagnetic radiation is continuous the intensity is at least 50 $\mu$Watts/cm$^2$ for treatment of eyes and mucous membranes, and more preferably is at least 500 $\mu$Watts/cm$^2$ for treatment of skin and up to 2 Watts/cm$^2$.

Preferably when the electromagnetic radiation is pulsed the intensity is at least 50 $\mu$Watts/cm$^2$ peak power for treatment of eyes and mucous membranes, and more preferably is at least 500 $\mu$Watts/cm$^2$ peak power for treatment of skin and the average power is up to 2 Watts/cm$^2$. The average power is the peak power multiplied by the proportion of the total time that the radiation is applied. For instance if the peak power is 500 $\mu$Watts/cm$^2$ and is pulsed for 10 $\mu$seconds at a frequency of 600 Hz then the average power is 30 $\mu$Watts/cm$^2$.

Preferably when the electromagnetic radiation is pulsed the average power of the intensity is in the region of 50-100 $\mu$Watts/cm$^2$.

We have found that the power may suitably range from 500 $\mu$Watts/cm$^2$ peak to 2 Watts/cm$^2$ continuous or peak power when applied to the skin. In the instance of applying electromagnetic radiation therapy to the eye or mucous membrane, powers as low as 50 $\mu$Watts/cm$^2$ continuous or pulsed are found to be beneficial. Typically 10 mWatts/cm$^2$ are used on skin but this value is dependent on how fat or muscular the subject is and thus how deep the tissue/area/organ to be treated may lie beneath the skin surface. Typically radiation of the intensity 5 mWatts/cm$^2$ is used on mucous membranes.

Preferably when the electromagnetic radiation is pulsed it is applied for pulse duration periods of at least 10-15 μseconds and more preferably is applied at a frequency/repetition rate in the range 480-800 Hz. More preferably still, the frequency/repetition rate is at, or about, 600 Hz.

Our studies have shown that the electromagnetic radiation can be either coherent or non-coherent the clinical outcomes are not affected by this parameter.

Preferably the electromagnetic radiation is applied to the affected area for at least 30 seconds and up to a few minutes. A typical exposure time for the skin or eye is in the region of 3 minutes, however for tissues well below the skin surface this time is increased according to the individuals fat/muscle layer depth and exposure could be up to 10 minutes.

It should be appreciated that the power source emitting the electromagnetic radiation will have to produce more than the required intensity for the clinical effect since we have shown that approximately 99% of the applied therapeutic amount of light is lost across the skin surface during treatment. Thus the intensity of applied radiation will have to be corrected for when carrying out a treatment.

Our studies have shown that the first clinical effects can be detected following 30 seconds of treatment for herpetic infections and that the majority of immediate clinical effects are experienced following 90 seconds of treatment. However certain tissues are more sensitive, for example the mucous membranes are exposed to the dosing regimen for approximately 30 seconds and immediate clinical effects are noted after only 3 seconds of treatment.

From the foregoing it is understood that the electromagnetic radiation may be directed to the target site either continuously or in a switched (pulsed) manner. The main benefit of switching enables power conservation and facilities much higher peak power output, thereby improving clinical response.

Preferably, electromagnetic radiation therapy system also includes means for reducing the amount of ambient radiation which impinges on the site of infection. The presence of ultraviolet light and violet light as in sunlight exacerbates herpetic conditions and it is preferred to exclude wavelengths below 400 nm. More preferably, wavelengths below 500 nm are excluded.

Preferably the system further includes means for fixing the intensity of the radiation within a pre-determined range. The radiation output may be monitored with a visible display indicating correct function of the device both for intensity and wavelength.

Preferably the system further includes means for controlling the duration of the application of the radiation. Accordingly, the present invention is concerned with the use of electromagnetic radiation having a wavelength in the range from visible to infra red and applied at a low intensity such that no thermal damage is caused to any human or animal tissues.

In the case where the system is to be used in such a way that radiation will be caused to enter the eye, it is preferred that the power intensity does not exceed 100 mWatts/cm$^2$. Otherwise, the power intensity may be higher and can suitably be delivered in pulsed form, thereby obtaining several watts of momentary power output, allowing good penetration of tissue and substantial systemic effect.

The radiation producing means are preferably solid state light emitting devices, more preferably solid state light emitting diodes or gas discharge devices. The radiation from such devices can be electrically operated or the radiation can be delivered to an applicator via a fibre-optic delivery system.

Preferably, the radiation emitter includes a PN junction arranged to emit radiation with a wavelength centring at or about 1072 nm or at or about 1268 nm. A single light diode assembly may include a plurality of orientated junctions.

Infrared emitting diodes may be arranged not only to emit radiation at a specific frequency but also to emit a high intensity divergent beam.

A gas discharge device may include a mixture of gases which will give an output at the desired wavelength, for instance, 1072 nm.

Another preferred radiation producing means is a laser diode device, an example being a laser diode emitting light at a frequency of 1064. nm. Such a light emitting means is of low power intensity having a divergent beam and not giving rise to thermal damage. It may be used to treat many conditions, including pain relief.

The present invention also provides the use of divergent electromagnetic radiation having a wavelength of between 980 and 1500 nm and an intensity of at least 50 μWatts/cm$^2$ and up to 2 Watts/cm$^2$ to treat an area of biological tissue of a living human or animal subject.

Preferably the electromagnetic radiation as produced by the system of the invention provides for treating conditions such as, without limitation, herpetic infections, bacterial and/or viral infections of the skin or upper respiratory tract, ophthalmic conditions such as "dry eye syndrome", caustic injuries, musculoskeletal conditions, inflammatory conditions such as rheumatoid arthritis and malignancies, reduction of scarring, promotion of wound healing, sports performance and providing acute and chronic pain relief.

The use of restricted bandwidth radiation can enhance the immune system as a result of which the body is able to combat infections, such as the herpes virus.

Although reference has been made to infections caused by the herpes virus, the present invention is not limited to such infections. It is applicable to other infections caused by all viruses including HIV, common cold and influenza viruses.

The present invention also provides a method of treating an area of biological tissue of a living human or animal subject comprising applying to said area divergent electromagnetic radiation having a wavelength of between 980 and 1500 nm at an intensity of at least 50 μWatts/cm$^2$ and up to 2 Watts/cm$^2$.

Preferably, the area to be treated is irradiated so that the affected tissue receives at least 50-500 μWatts/cm$^2$ peak power of radiant energy, depending on the tissue to be treated. A factor here is the period of irradiation and, preferably, the period should be at least a specified minimum of 10-15 μseconds at a repetition rate/frequency of 450-800 Hz and preferably for at least 30 seconds duration.

BRIEF DESCRIPTION OF THE DRAWINGS

Embodiments of the invention will now be described, by way of examples only, and with reference to the accompanying drawings, in which:—

DETAILED DESCRIPTION OF PREFERRED EMBODIMENTS

Referring to FIGS. 1 to 4, a first embodiment in accordance with the present invention includes a hand held divergent narrow wavelength radiation source 4 with a built in timer and ambient radiation detector. A single wavelength is used at any one time, preferably in the infrared spectrum. However, the effective wavelengths, which may be covered by such a device, extend from the visible spectrum to the infrared. In another embodiment of the invention, two wavelengths are used, one that is visible and the other that is invisible, particularly in the case where the optimal wavelength is in the infrared.

Radiation source 4 includes an elongate, rectangular cross-section hollow body with one end 8 being transparent to light. The radiation source includes an array of light emitting diodes 2 mounted close to transparent end 8. Power is delivered to devices 2 by means of batteries 3 located within hollow 3 of the body 4.

The radiation source is provided with two On/Off switches 5, which may be actuated to initiate the operation of the internal electronics. Both buttons 5 have to be pressed simultaneously in order to operate the device correctly, thereby preventing inadvertent use of the device. Close to the end opposite transparent end 8 is a utility hole 6 which allows the radiation source to be hung up or attached to another article such as a bunch of keys.

The radiation source is provided with control electronics, which limit the time that the radiation source is on and then automatically switches off the radiation source. The control electronics monitor the ambient radiation and, in the event that the ambient radiation is of an intensity that would interfere with the therapeutic effect of the radiation source, an alarm buzzer (not shown) sounds. The radiation emitting devices 2 and their location and arrangement within the radiation source are such that the radiation emitted from the radiation source is in the form of a divergent light beam. Flange 1 restricts the ambient radiation incident on the area whilst being treated.

The radiation therapy system of the present invention could be adapted to be portable and for use by those individuals wishing to have their own self-contained and battery operated devices. Additionally it could be adapted so that during use an animal or human appendage could be located within a hollow body 3 to receive radiation emitted therefrom. This particular modification is particularly suited to treatment of genital herpes around the scrotal sac and/or penis.

Figure 1:
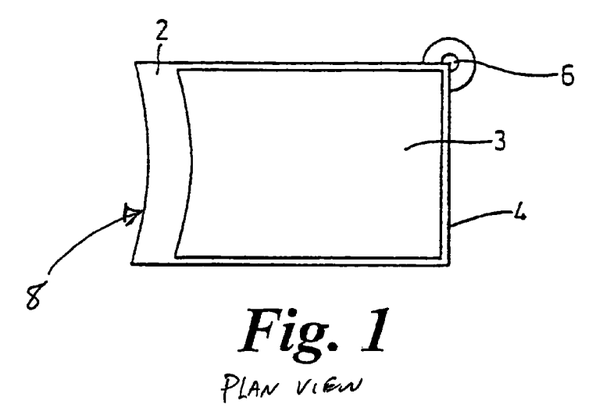
FIGS. 1 to 4 are a view with cover removed, side view, under view and front view respectively of a first embodiment in accordance with the present invention.
Figure 2:
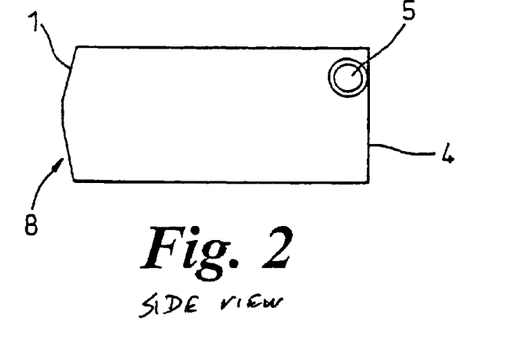
Figure 3:
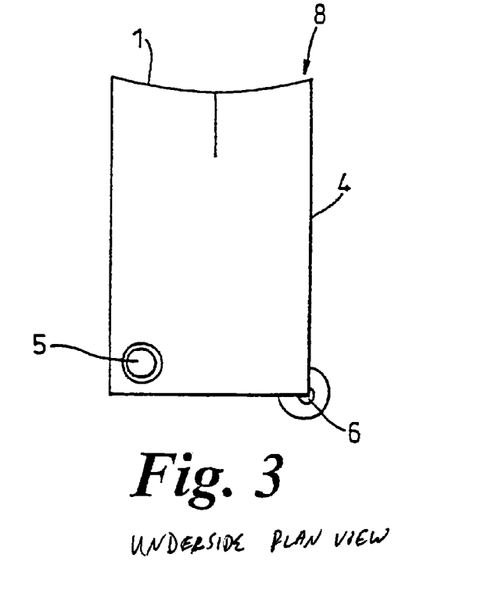
Figure 4:
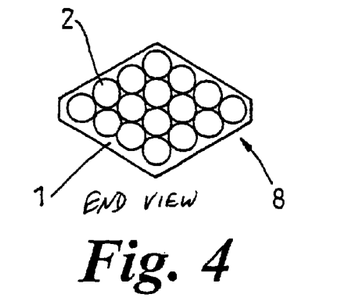
Figure 5:
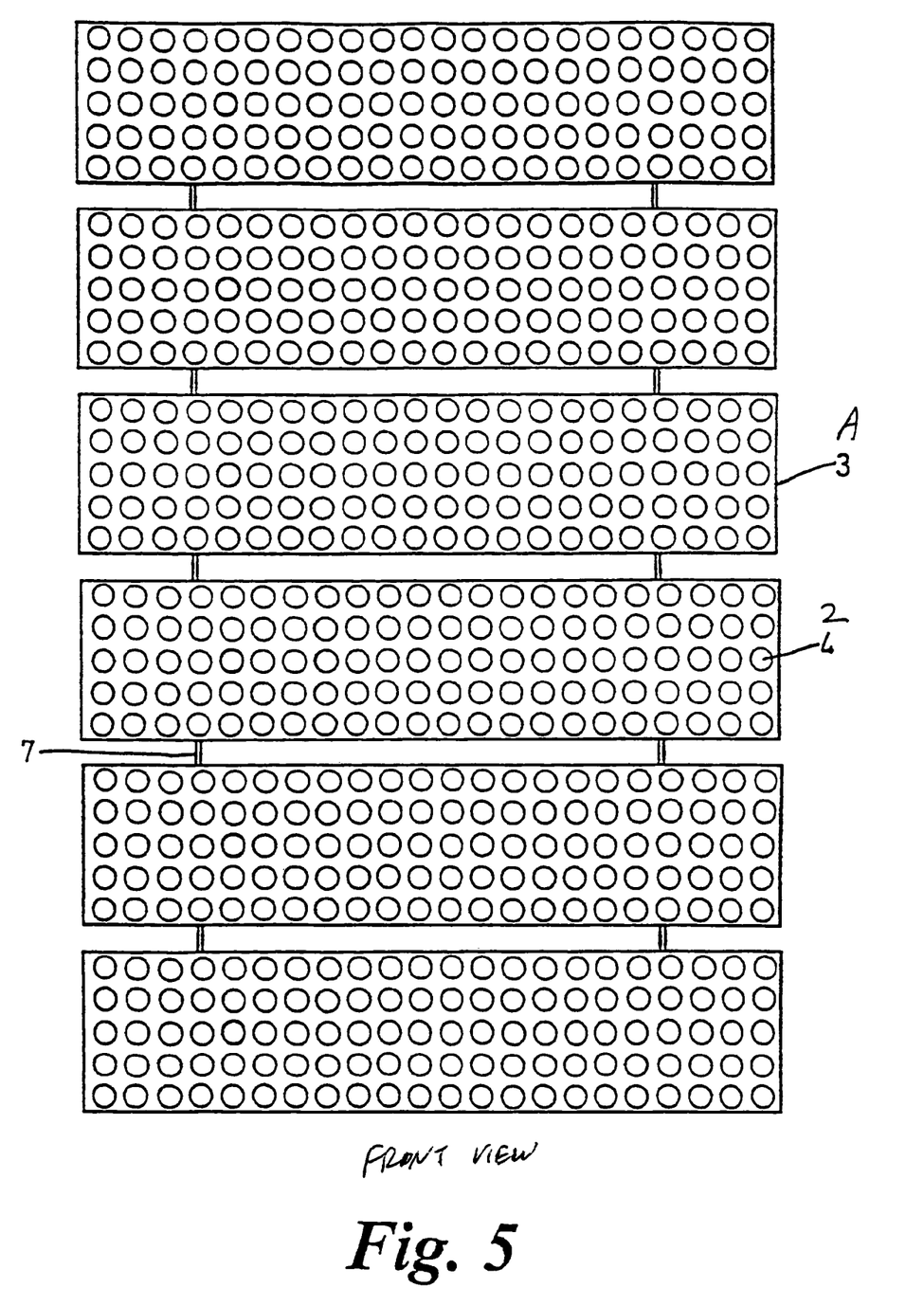
FIGS. 5 to 7 are a front view, top view and under view of a second embodiment in accordance with the present invention.
Figure 6:
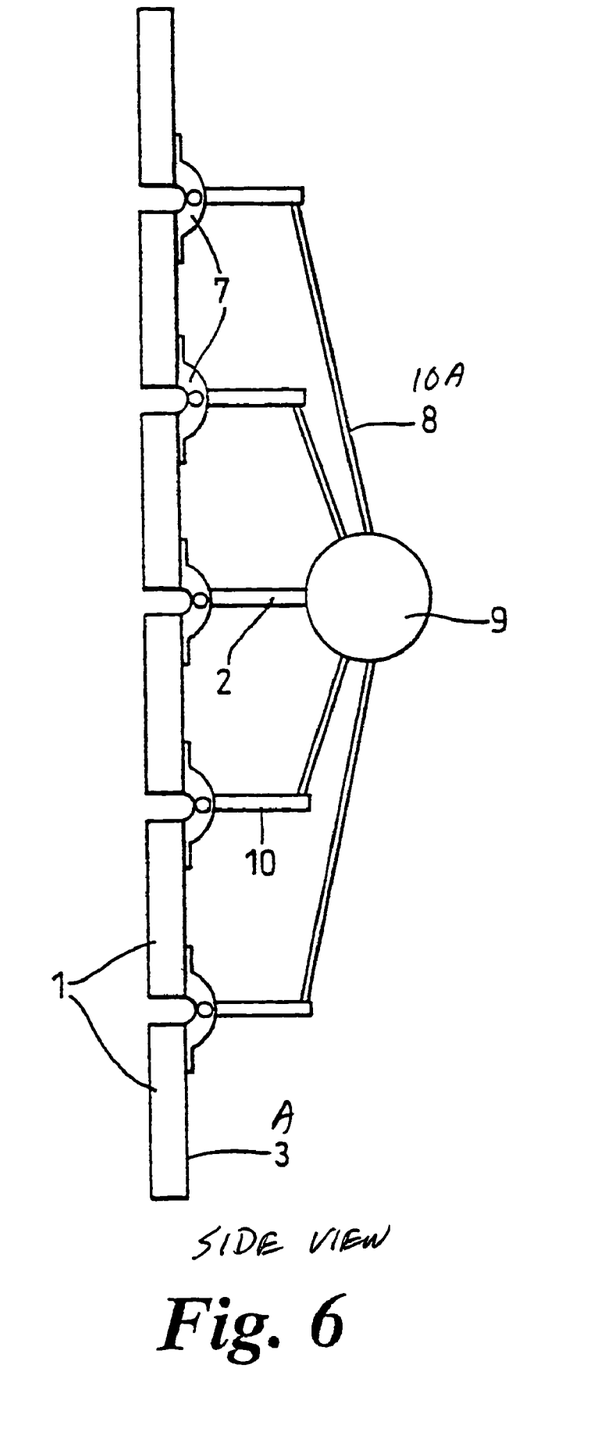
Figure 7:
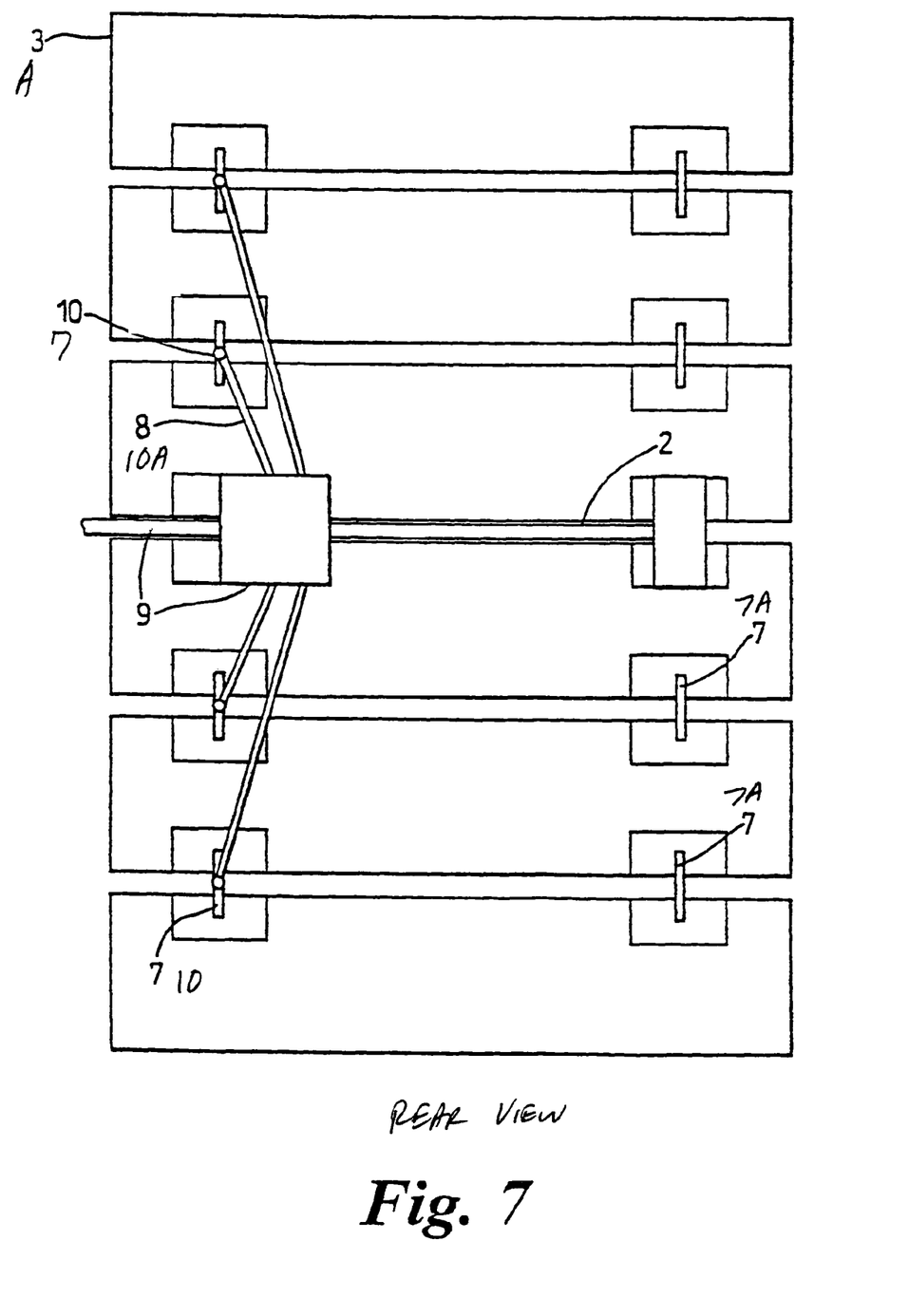

Referring to FIGS. 5 to 7 of the accompanying drawings, a second embodiment in accordance with the present invention is in the form of a multi-panel narrow wavelength radiation source. In this case, a plurality of panels A are mounted in a side by side relationship on hinges 7 and 7A which, in turn, are connected to a stand 9 by means of arms 10 and 10A. The arrangement is such that the panels can move relative to each other and the stand can be adjusted to alter the direction of illumination. The stand either extends from the floor or is attached to a chair or bed.

The front wall of each panel A is transparent and, mounted below the front wall, is an array of radiation emitting devices 2.

As with the earlier above described embodiments this embodiment of the invention includes control electronics to limit the time of the application of the radiation and to monitor the ambient radiation and provide an alarm when the threshold value of the ambient radiation is exceeded.

Figure 8:
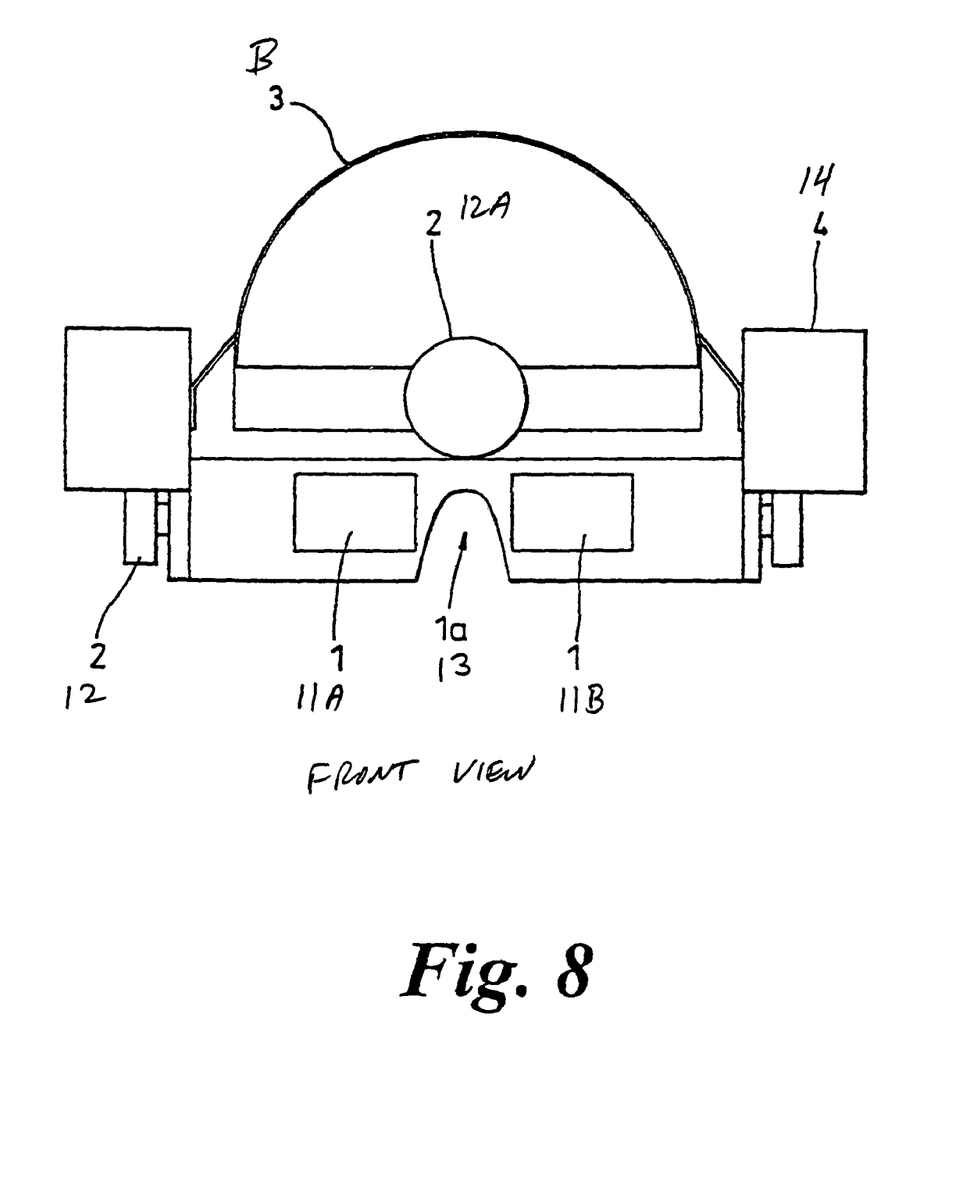
FIGS. 8 to 10 are a back view, top view and a side view of a third embodiment of the present invention.
Figure 9:
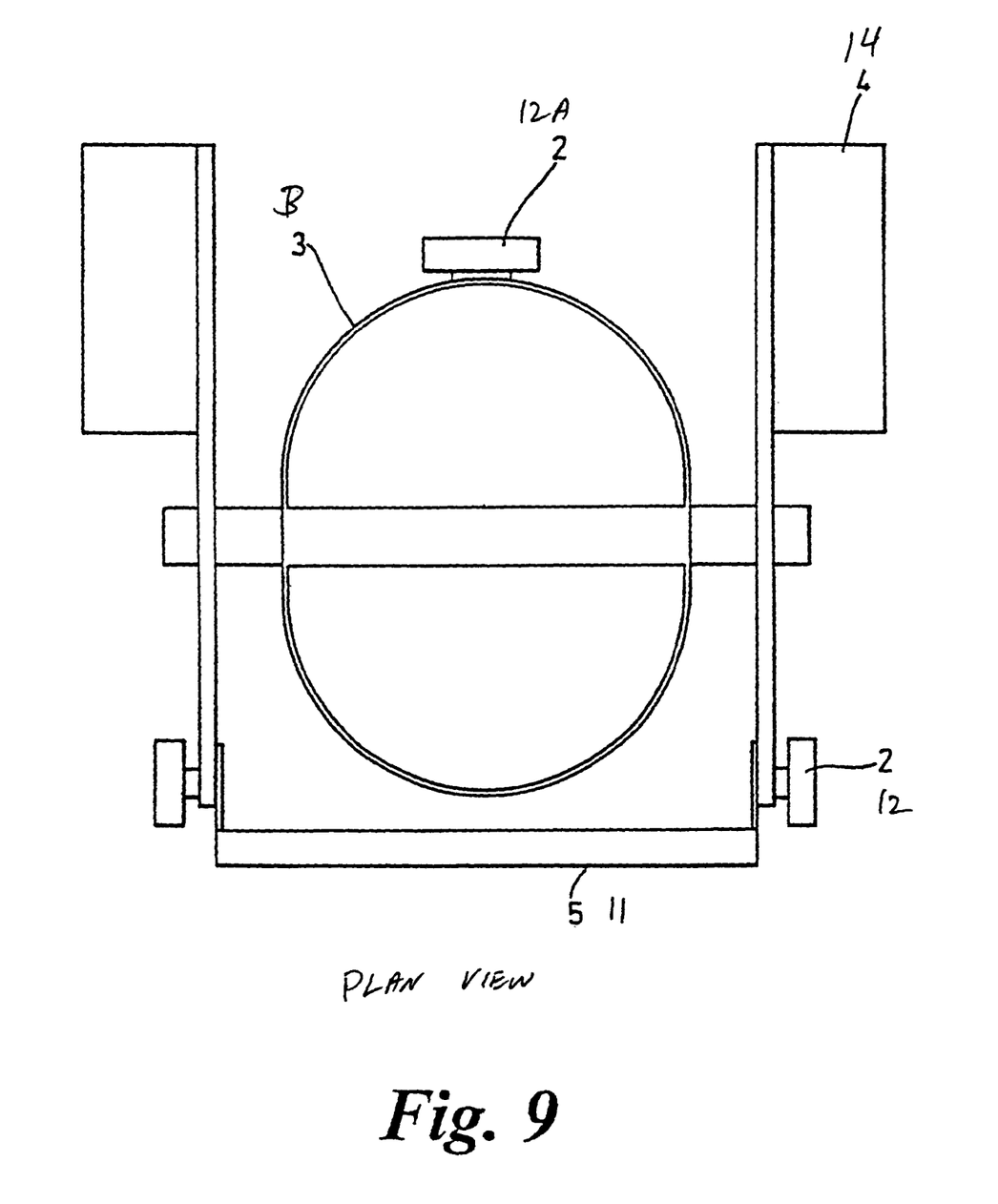
Figure 10:
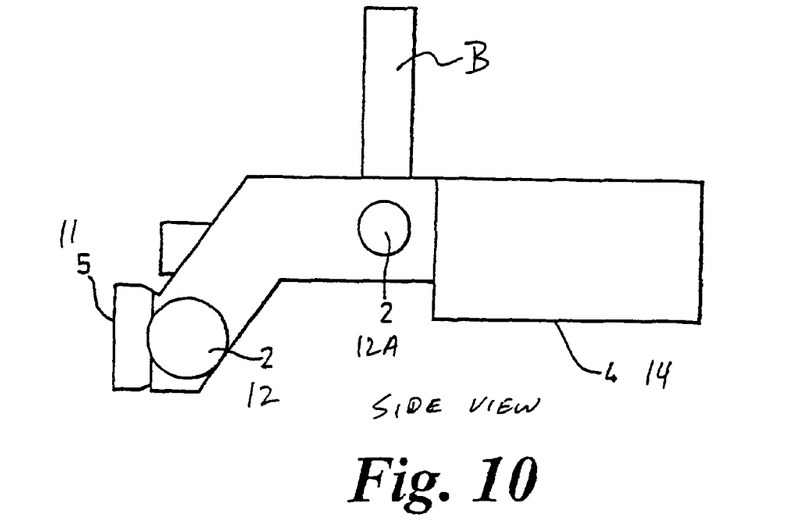

Referring to FIGS. 8 to 10 of the drawings, a third embodiment in accordance with the present invention is in the form of a narrow wavelength radiation source with adjustable headgear.

Flange 1 excludes ambient light if the device is in contact with the body.

The radiation source is, in use, located on the operator's head by a band or helmet B and includes two panels 11A and 11B of radiation emitting devices, panels 11A and 11B being separated by an intervening notch 13. These radiation panels 11A and 11B can be used either simultaneously or separately, there being provided a switch (not shown) to direct electrical power to one or both of panels.

The radiation panels 11A and 11B are held close to the eyes by adjustable control elements 12A and 12B.

The radiation source is provided with control electronics 4, which limit the time of application of the photons to the affected site and also automatically switch off the radiation at the end of the application period. As before the control electronics monitor the ambient radiation and provide an alarm when the threshold level is exceeded.

Figure 11:
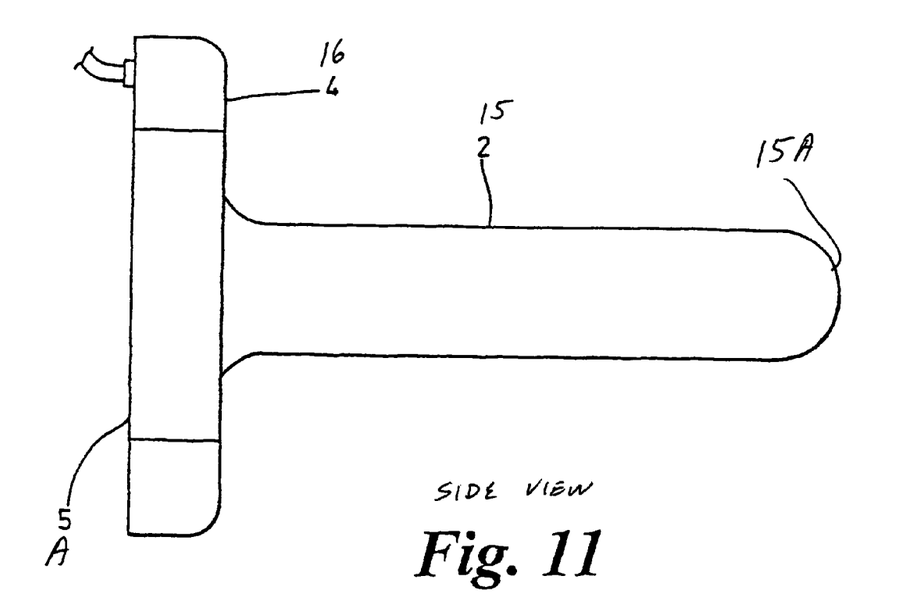
FIGS. 11 and 12 are a side view and a view from the right (as seen in FIG. 11) of a fourth embodiment in accordance with the present invention.
Figure 12:
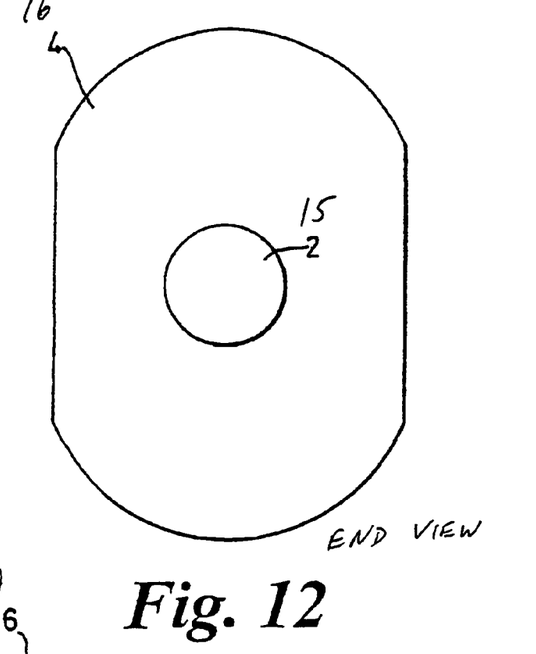

Referring to FIGS. 11 and 12 of the accompanying drawings, a fourth embodiment of the present invention is in the form of a narrow or restricted bandwidth radiation source for delivery of photons to an orifice. In this case the body of the radiation source includes an elongate cylindrical portion 15 having at one end a flange 4 whose shape is indicated in FIG. 12. At its other end, elongate portion 15 is hemispherical 15A. Radiation emitting devices are located both in the elongate portion 15 and the flange 16 and this radiation source can be used to deliver photons to any orifice in the human/animal body, for instance, the vagina, anus, oro and nasopharynx and buccal cavity. The radiation source may be provided in different sizes according to the size of the orifice into which it is to be inserted.

Control electronics limit the time of irradiation and monitor the ambient radiation, as with the previously described embodiments of the invention.

Figure 13:
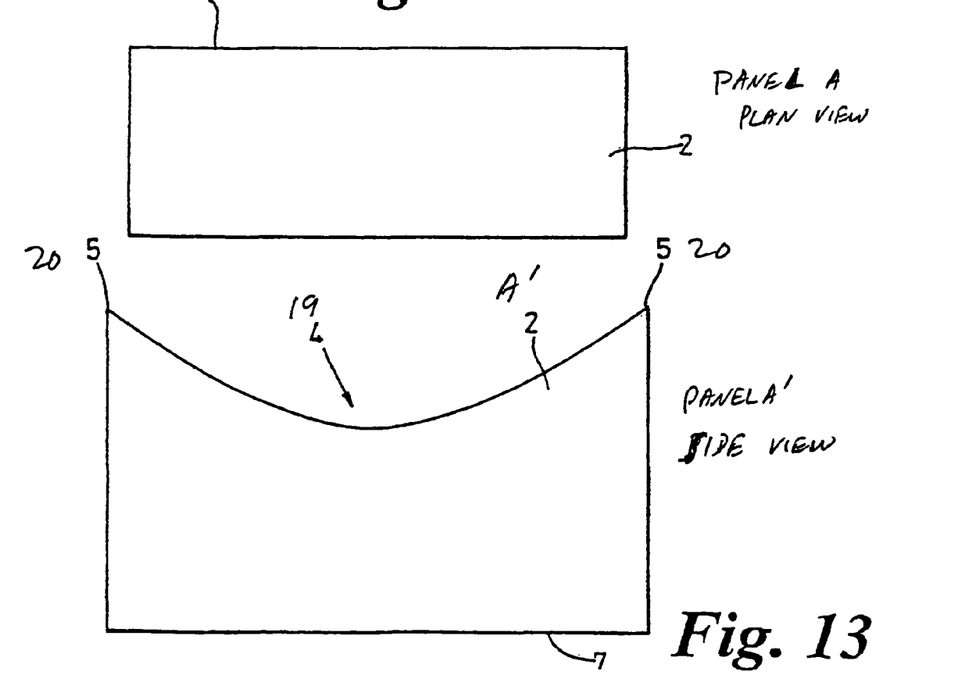
FIGS. 13 and 14 show further embodiments of the present invention.
Figure 14:
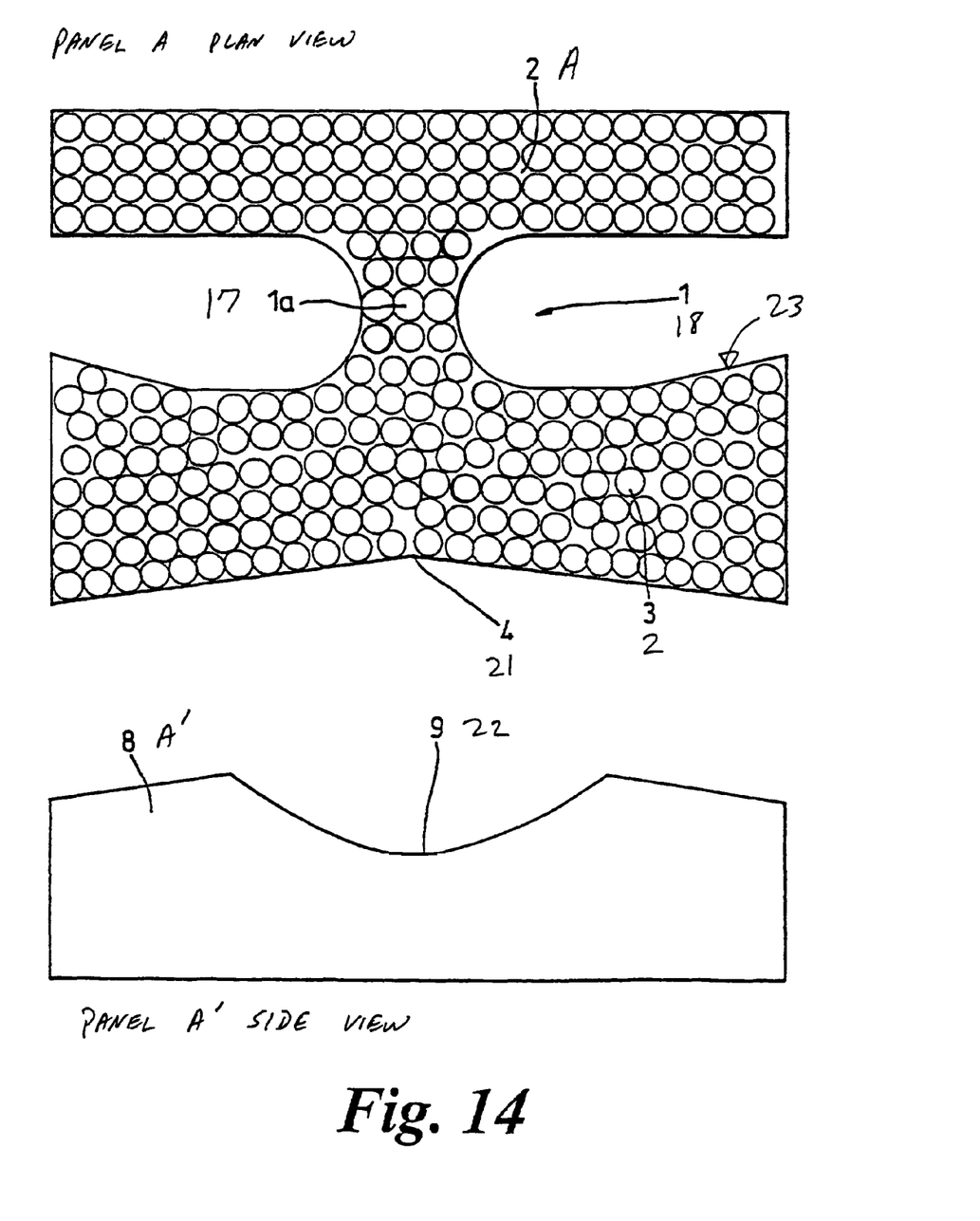

FIGS. 13 and 14 illustrate devices useful in the treatment of the common cold and acne.

The common cold is caused by a viral infection of the upper respiratory tract. The viral particles are almost exclusively found in the pharynx, sinuses and nasal passages.

The device is a radiation emitting apparatus, which delivers a narrow bandwidth radiation, which, is of a wavelength, that will penetrate the superficial skin and penetrate the underlying tissue to sufficient extent to generate a therapeutic effect.

The device in FIG. 14 is flexible and is placed against the patient's face whilst he is lying supine. Notch 18 provides an aperture for the patient's eyes. Panel A provides treatment for the frontal sinuses. Panel A' provides treatment for the maxillary sinuses and nose, and the intervening bridge 17 provides treatment for ethmoid sinuses and nose.

The device in FIG. 13 is a flexible radiation emitting apparatus, which is placed against the patient's neck so that the points 20 approximate the base of the patient's ears. This apparatus delivers radiation for therapeutic effect to the patients larynx, oropharynx and laryngopharynx. Depression 19 fits underneath the patient's chin.

Devices for treating acne are as shown in FIGS. 13 and 14 and comprise several panels of variable shape and size. All the panels have a radiation emitting device 2 and are flexible to enable the panel to follow the contour of the face and neck. Panels A and A' (FIG. 13) are applied to the inferior aspect of the chin and the neck respectively.

Panels A and A' in the FIG. 14 device are applied to the face so that notch 1 enables the patient to see whilst being treated. Bridge 17 treats the bridge of the nose and extension 2 the cheeks. Notch 21 rests on the tip of the nose allowing the patient to breathe comfortably during treatment. Panel A' is used to treat the chin area and the area at notch 22 adjacent to the mouth.

Where the chest and/or back is involved a larger version of panel A would be used as in FIG. 5.

Due to the superficial nature of the pathology ambient radiation is of significance and an ambient radiation detector is utilised.

Treatment time is at most 10 minutes but typically 5 minutes.

It should be appreciated that two or more of the above-described devices can be used in conjunction with one another. An example is in the treatment of paediatric herpetic stomatitis where the device for delivery of radiation to an orifice could be used in conjunction with the multipanel device to ensure adequate delivery of the radiation system.

The application of radiation in the manner described appears to give the patient immediate (within 6 minutes) relief from any pain which is chemically mediated irrespective of the inflammatory condition causing it i.e. it gives pain relief in conditions other than those caused by viral infections. It does not affect the conduction of pain impulses as in local anaesthetics.

Experimental Results

Examples of the invention will now be described with reference to the treatment of particular conditions.

Herpes

The radiation-emitting surface was placed against the cold sore for at least 90 seconds, typically 4 minutes. The environmental conditions must be such that the ambient radiation to the cold sore must be decreased below acceptable levels. This can be achieved either by switching the radiation off or designing the device with a flange around the outside, diminishing the ultraviolet light to the area. Treatment is only once a day. One treatment may be all that is necessary however, in view of the fact that this also enhances wound regeneration and the wound regenerative effect only lasts 24 hours, daily treatments would improve clinical response. Various wavelengths were evaluated using a double blind control trial, Zovirax® being given to the control patients. The average time for patient to be treated with 660 nm radiation took 7.5 days. The average time for a patient to be treated with 1072 nm radiation was 3 days if lesion was already present. However it was less than 12 hours if the patient only has a tingling sensation.

99.5% of patients abort their attack if they are treated within the tingling period using 1072 nm radiation. The cure rate of the patients receiving radiation treatment was total, in that none had a recurrence of their cold sores at the site treated. However 20% of the acyclovir treated group had recurrence at the site of treatment.

The number in the trial was 300.

A further study was conducted in a double blind protocol comparing radiation treatment to acyclovir. The group receiving radiation therapy had cold sores that healed within 4.7 days and the group receiving acyclovir had cold sores that healed within 4.7 days. Statistical analysis resulted in a p value of 0.027, which was statistically significant.

Please refer to the table below for further details.

| Treatment | Number of Patients | Mean Time to Healing (days) |
| --- | --- | --- |
| Placebo radiation plus acyclovir | 14 | 6.9 |
| Active radiation | 15 | 4.7 |
| Active radiation plus placebo cream | 16 | 6.7 |
| Acyclovir | 18 | 8.5 |
| Red Light | 20 | 7.5 |

Genital Herpes

Again the applicator was required to follow the contours of the genitals and for a woman the cervix and posterior fornix was treated simultaneously with vagina and perineum. The treatment period is only 4 minutes. Due to the shape of the device, ambient radiation is excluded from the treatment area, and darkened room is not necessary.

A total of eight patients have been treated, all of who have reported a shorter duration of their recurrent attacks of genital herpes. In addition, after one year of treatment, for each attack, all patients have been free from recurrence for the last 6 months, whereas they typically had an attack per month.

Shingles

The radiation panel was applied to the area that is infected, for periods of 4 minutes. If the panel is applied to the actual skin surface and the panel is optically opaque it will occlude the ambient radiation from the area and hence allow treatment to proceed successfully. The only exception where a darkened room is essential is for the treatment of ophthalmic conditions when one cannot have the radiation-emitting surface close to the eye because of the generation of heat. The generation of heat in association with ophthalmic conditions is contraindicated. A helmet was used with an ambient radiation detector with alarm so that the radiation can be delivered to the orbital region. Again the treatment period was 4 minutes. Generally ophthalmic conditions are treated on a daily basis. However, ophthalmic herpes can be treated once every three days to achieve a positive result.

Four patients have been treated; all of who had significantly shortened healing periods and decreased incidence or recurrence.

The Common Cold

The patient was reclined on a bed, preferably in subdued lighting, but this is not essential. The device was placed against the skin ensuring that the frontal, ethmoidal and maxillary sinuses are covered. Another panel was placed again the neck, ensuring that the device goes as high as the angle of the jaw to enable treatment of the pharynx and larynx areas. The treatment cycle is at least 4 minutes. After that has been completed an oral device was used which is very similar to the vaginal applicator without the flange. The device was inserted into the patient's mouth. The treatment period was again for 4 minutes. This applicator has a disposable outer skin, which is changed with each patient. The applicator will treat the soft palate and the back of the oral pharynx and the top of the nasopharynx where the surface applicator would not achieve acceptable penetration levels. Using this protocol alleviation of the pain associated with pharyngitis was achieved immediately, i.e. within 90 seconds, and the symptoms associated with oral pharyngitis have been alleviated within six hours.

Ten patients have been treated. Of note is that unrestricted light can be applied to the pharynx with immediate relief of symptoms, however for improved efficacy, light of the wavelength 1072 nm is required to be applied to the face and sinuses. We noted that in all cases the sore throat was improved immediately and symptoms of congestion and flu-like illness were alleviated in 4-6 hours.

Acne

Using the same applicator adolescent acne can be treated by the simple addition of a chin extension. The treatment time is 4 minutes. Ambient light is important but not in as much as the applicator will have an opaque surface so therefore it will be sheer proximity to the skin reduce ambient light to the skin. Applications should initially be every two to three days and maintenance would be perhaps once a week.

Twelve patients have successfully been treated with light of the light therapy system. Results indicate that if 950 nm 5 mm diodes were used there was a marked exacerbation of the disease process, however when using 950 nm 8 mm diodes there was a slight increase in inflammation but an overall improvement. The use of restricted radiation resulted in a rapid resolution of acne over 7 days. Daily treatment enhanced clinical results. Once a clinical result was achieved, the regimen was maintained for 1-2 treatments per week for a satisfactory outcome.

Musculoskeletal Disorders

Treatment of musculoskeletal disorders such as tennis elbow gout, muscle injuries and knee injuries. The application time again is only 4 minutes. The radiation is directed over the affected area and gentle pressure is applied. Once the treatment is complete the patient feels immediate pain relief and improved joint movement. Muscle stiffness is greatly improved. This is a distinct advantage in the treatment of gout since this can be an extremely painful condition. The treatment could be repeated after 24 hours. Generally speaking treating prior the 24 hours is not indicated, as there is no additional clinical benefit.

Post-Operative Wounds 24 hours after an operation, a 4-minute treatment period reduces pain for 6-8 hours and this was repeated three to four times a day to enhance would healing. The treatment may be used on a daily basis with or without the pain for post-operative wounds.

Seven volunteers, all of whom had minor surgery found decreased scar formation if the area of surgical incision was treated daily for 10 days commencing on the day of surgery. Thus it is envisaged that the present invention has applications in the treatment of keloids, burns and cosmetic surgery.

Connective Tissue Diseases

Rheumatoid arthritis is an example of this group of conditions. The painful areas are treated in a device which comprises one fixed panel in which the hands are placed on and a flexi panel which is placed over the top of the hands applying gentle pressure to aid additional penetration of the skin. The treatment time is 4 minutes. Ambient radiation does not appear to be a significant factor in the treatment of rheumatoid arthritis. Part of the treatment protocol can also be in the treatment of thymus, liver and regional lymph nodes, which are all associated with antigen recognition. Again treatment time is 4 minutes. The thymus, lymph nodes, liver and spleen may be treated once a week, whereas the hands may be treated initially once a week. However, during an acute exacerbation they can be treated daily. If treated more than once daily there appears to be no advantage.

A small trial involving eight patients in the Rheumatology Clinic resulted in the findings that those receiving placebo radiation treatment felt more relief than those patients receiving active 950 nm radiation. However, when using radiation in the restricted wavelength according to the present invention, all ten patients reported a clinical benefit compared to the placebo treatment. In addition we found that if the thymus and other aspects of the reticuloendothelial system were treated with the restricted radiation the patients experienced an overall cessation of their arthralgia and myalgia.

Malignancy

The area of the tumour is treated together with treatment to the antigen recognition centres such as thymus, spleen, liver and lymph nodes. Daily whole body treatments may be carried out.

Bacterial Infections

A number of diverse minor bacterial infections have been treated successfully in 35 patients. In all cases the infection had been present for at least three days and was considered to be worsening daily. At the time of treatment each patient would have ordinarily been prescribed an oral antibiotic. In 70% of cases the infection was resolving 6 hours after treatment and was completely better within one day. In the remaining 30% of cases the infection had improved considerably within one day and following a second radiation treatment, the infection was gone by the second day. Of clinical note was the observation that in the Caucasians treated there was a significant decrease in superficial scar tissue at the site of assault. As previously noted, the 8 mm 950 nm diode unrestricted radiation source was effective but not as effective as the restricted radiation of 1072 nm of the present invention.

Sports Medicine

Treating all muscle groups prior to training will increase the level to which the athlete can train by as much as 50%, in addition to decreasing the incidence of muscle injury.

In a double blind trial, five volunteers were used by treating one limb with placebo radiation and the corresponding other limb with active radiation. In all cases the volunteers were able to increase their effort tolerance before feeling muscle fatigue by 30-50% in the limb treated with the active radiation.

Muscle injuries have been successfully treated in 35 patients. The pathology involved included rotor cuff syndrome, tennis elbow, lower back pain and lumbar fascitis. The response to therapy ranged from immediate relief in 30% of cases to complete relief after 24 hours in the remaining 70%. Daily treatment is required until the problem is resolved.

Ophthalmic Conditions

Chronic ophthalmic pain was successfully alleviated permanently in 90% of the eleven patients treated.

Unstable corneal epithelium (over a period of 6 weeks) which resulted in recurrent corneal ulceration, was stabilised in 6 patients promoting an intact corneal surface within 5 days of commencement of daily treatments of radiation therapy.

Four patients with conjunctivitis sicca or dry eye syndrome, reported significantly decreased eye irritation and produced significantly less debris accumulation within fornices following radiation treatment. Of note was the experience that whilst radiation centred on 1072 nm was effective in this condition, radiation centred on 1268 nm was more effective. Once weekly treatment with radiation was sufficient to alleviate symptoms.

Episcleritis and other inflammatory conditions of the eye were successfully treated in 11 patients. Daily treatments were necessary to obtain the desired clinical effect. The recurrence of the inflammatory condition was decreased in all cases. All patients treated had suffered their conditions over several months and resolution occurred in 3-4 days without the use of eye drops.

Severe caustic injury to the eye is considered untreatable and almost always results in destruction of the cornea and blindness. Animal experiments (conducted in South Africa) have indicated that caustic injury is treatable with the radiation of the present invention.

Five pairs of rabbit eyes were exposed to a supersaturated solution of NaOH for 30 seconds after topical administration of an anaesthetic. All eyes were washed out thoroughly following the caustic injury and it was noted that the corneas were immediately opaque following the injury. One eye of each rabbit was then either treated with conventional steroids plus antibiotic whilst the other eye was treated with the radiation of the present invention. All rabbits were sacrificed 4 weeks following twice daily treatment. In all cases the eyes that had been treated with conventional therapy (steroids plus antibiotic) rapidly developed panophthalmilitis with resulting blindness, whilst the eyes treated with the radiation therapy of the invention showed that the anterior chamber, lens, vitreous and retina were intact despite corneal damage. In addition the scar tissue in the radiation treated eyes was reduced by at least 50% compared to the conventionally treated eyes.

Further experiments involving a less concentrated solution of NaOH being applied for a longer duration, 3 minutes, resulted in corneal damage to all eyes as gauged by pale milky appearance to the corneas. The same protocol of treatment was applied, I.E. one eye being treated in conventional manner and the other by radiation therapy. The animal were sacrificed following two weeks of treatment and the results showed that eyes treated with the radiation therapy were clear whilst the conventionally treated eyes remained opaque.

The ability to reduce scarring was investigated using 5 pairs of rabbit eyes. Each eye was scarred by a 4 mm linear full thickness incision in the centre of the corneas under topical anaesthesia. One eye was treated conventionally and the other by radiation therapy. All eyes healed however the eyes receiving radiation therapy healed at a faster rate with scarring reduced by 50%. It was noted that radiation centered on 1072 nm gave best similar results.

Pain

Radiation at 950 nm was only marginally effective compared to the restricted radiation at 1072 and 1268 nm. It was noted that 1072 nm was more effective than 1268 nm radiation in treatment of acute pain as caused by a superficial burn However, 1268 nm radiation was reported as more effective at alleviating deep muscle pain caused by muscle injury.

Pain was gauged in patients by subjective assessment.

Thus it will be appreciated that the radiation therapy system of the present invention has wide application in treating a variety of different diseases and conditions. The radiation therapy system effects on a patient are rapidly felt and since the system is non-invasive it presents a less stressful/traumatic therapy to the patient. Moreover, the system could be used to treat a wide variety of patients quickly thus reducing the financial burden to the health service.

The invention claimed is:

1. A method for treating and/or improving herpetically infected body tissues, the method comprising:
    exposing the herpetically infected body tissue to divergent electromagnetic radiation at a wavelength restricted to a peak wavelength of 1072 nm so as to coincide with peak transmissions of a water molecule; and
    selecting a radiation intensity for the electromagnetic radiation capable of producing, at the site of the herpetically infected tissue, a radiation intensity of at least 50 $\mu$Watts/cm$^2$ up to 2 Watts/cm$^2$.

2. The method of claim 1, further comprising selecting the half angle divergence of the electromagnetic radiation in the range 15° to 45°.

3. The method of claim 1, wherein the electromagnetic radiation is pulsed.

4. The method of claim 1, wherein the electromagnetic radiation is continuous.

5. The method of claim 4, wherein the tissue comprises eye, and/or mucous membranes, or combinations thereof.

6. The method of claim 4, wherein selecting a radiation intensity further comprises selecting a radiation intensity of at least 500 $\mu$Watts/cm$^2$ and up to 2 Watts/cm$^2$, wherein the tissue comprises skin tissue.

7. The method of claim 1, wherein exposing the tissue to the selected electromagnetic radiation includes exposing herpetic virally infected tissue to the selected electromagnetic radiation resulting in alleviation of the herpetic viral infection.

8. The method of claim 1, further comprising:
    monitoring the electromagnetic radiation; and
    indicating the intensity and wavelength of the electromagnetic radiation.

9. A method for treating and/or improving bacterially infected body tissues, the method comprising:
    exposing bacterially infected tissue to divergent electromagnetic radiation at a wavelength restricted to a peak wavelength of 1072 nm so as to coincide with peak transmissions of a water molecule; and
    selecting a radiation intensity for the electromagnetic radiation capable of producing, at the site of the tissue, a radiation intensity of at least 50 $\mu$Watts/cm$^2$ up to 2 Watts/cm$^2$.

10. The method of claim 9, further comprising selecting the half angle divergence of the electromagnetic radiation in the range 15° to 45°.

11. The method of claim 9, wherein the electromagnetic radiation is pulsed.

12. The method of claim 9, wherein the electromagnetic radiation is continuous.

13. The method of claim 12, wherein the tissue comprises eye, and/or mucous membranes, or combinations thereof.

14. The method of claim 12, wherein selecting a radiation intensity further comprises selecting a radiation intensity of at least 500 $\mu$Watts/cm$^2$ and up to 2 Watts/cm$^2$, wherein the tissue comprises skin tissue.

15. The method of claim 9, wherein exposing the tissue to the selected electromagnetic radiation includes exposing bacterially infected tissue to the selected electromagnetic radiation resulting in alleviation of the bacterial infection.

16. The method of claim 9, further comprising:
    monitoring the electromagnetic radiation; and
    indicating the intensity and wavelength of the electromagnetic radiation.

17. A method for treating and/or improving bacterially infected body tissues, the method comprising:
    selecting a frequency of divergent electromagnetic radiation at a wavelength restricted to a peak wavelength of 1072 nm so as to coincide with peak transmissions of a water molecule;
    selecting a radiation intensity for the electromagnetic radiation capable of producing, at the site of the tissue, a radiation intensity of at least 50 $\mu$Watts/cm$^2$ up to 2 Watts/cm$^2$; and exposing the bacterially infected tissue to the selected electromagnetic radiation.

18. The method of claim 17, further comprising selecting the half angle divergence of the electromagnetic radiation in the range 15° to 45°.

19. The method of claim 18, wherein the electromagnetic radiation is pulsed.

20. The method of claim 19, wherein selecting a radiation intensity further comprises selecting a radiation intensity of at least 50 μWatts/cm$^2$ peak power and having an average power of up to 2 Watts/cm$^2$, wherein the tissue comprises eye, and/or mucous membranes or combinations thereof.

21. The method of claim 19, wherein selecting a radiation intensity further comprises selecting a radiation intensity of at least 500 μWatts/cm$^2$ peak power having an average power up to 2 Watts/cm$^2$, wherein the tissue comprises skin tissue.

22. The method of claim 19, wherein selecting a radiation intensity further comprises selecting an average power of the radiation intensity in the region of 50-100 μWatts/cm$^2$.

23. The method of claim 18, wherein the electromagnetic radiation is continuous.

24. The method of claim 23, wherein the tissue comprises eye, and/or mucous membranes or combinations thereof.

25. The method of claim 23, wherein selecting a radiation intensity further comprises selecting a radiation intensity of at least 500 μWatts/cm$^2$ and up to 2 Watts/cm$^2$, wherein the tissue comprises skin tissue.

26. The method of claim 17, further comprising:
  monitoring the electromagnetic radiation; and
  indicating the intensity and wavelength of the electromagnetic radiation.

27. The method of claim 17, wherein exposing the tissue to the selected electromagnetic radiation includes exposing bacterially infected tissue to the selected electromagnetic radiation resulting in alleviation of the bacterial infection.

* * * * *